United States Patent [19]

Chiba

[11] Patent Number: 4,874,137
[45] Date of Patent: Oct. 17, 1989

[54] ULTRASONIC CELL-DESTROYER

[76] Inventor: Shigeru Chiba, WACORE Yoshino-cho Garden 110, 319-3 Nakamura-cho 5-chome, Minami-ku, Yokohama-shi, Kanagawa-ken, Japan

[21] Appl. No.: 270,217

[22] Filed: Nov. 14, 1988

[30] Foreign Application Priority Data

Aug. 1, 1988 [JP] Japan .................................. 63-192223

[51] Int. Cl.$^4$ ............................................. B02C 19/18
[52] U.S. Cl. ......................................... 241/301; 241/1; 241/2; 241/21
[58] Field of Search ................. 241/1, 2, 21, 301, 46 R

[56] References Cited

U.S. PATENT DOCUMENTS 2,738,172  3/1956  Spiess et al. .......................... 241/1 X
4,295,613  10/1981 Moore et al. ........................... 241/2
4,697,751  10/1987 Chiba .................................. 241/1 X

FOREIGN PATENT DOCUMENTS 55756  4/1983  Japan ....................................... 241/1

Primary Examiner—Mark Rosenbaum
Attorney, Agent, or Firm—Cushman, Darby & Cushman

[57] ABSTRACT

Disclosed is an ultrasonic cell-destroyer using cell-suspending solution containers each having a groove at its bottom, thereby causing ultrasonic energy available to converge to the container bottom to increase the efficiency at which cells can be destroyed in the cell-suspending solution. The ultrasonic cell-destroyer may use a rotary container holder, which is capable of rotating a plurality of containers in the bath to evenly expose all the containers to ultrasonic wave.

7 Claims, 7 Drawing Sheets

ULTRASONIC CELL-DESTROYER

BACKGROUND OF THE INVENTION

1. Field of the Invention

The present invention relates to an ultrasonic cell-destroyer, and particularly to an apparatus for destroying cells floating in a solution in a closed container by radiating ultrasonic wave to the solution in the container, thereby subjecting the floating cells to impacts and/or cavitations caused by the radiation of ultrasonic wave and destroying them.

2. Description of the Prior Art

Recently in medical science, agricultural and forticultural chemistry and other science fields biochemical analysis has been popular, and accordingly there is an ever increasing demand for destruction of cells. In general, destruction of cells means that the outer membrane of each cell is broken to remove its minute organs.

Sometimes, destruction of cells means that the minute organs of the cells are destroyed. An ultrasonic cell-destroyer has been used for the purpose. In a conventional ultrasonic cell-destroyer and ultrasonic generator horn or tip is soaked in the cell-suspended solution in an open container, such as test glass or test cup. Then, the vibrator of the ultrasonic generator is vibrated by an associated high-frequency oscillator, thereby subjecting the cells to the radiation of the ultrasonic wave in the solution so that their membranes may be broken by force caused by cavitation.

Advantageously in this conventional ultrasonic cell-destroyer, a lot of similar cells can be destroyed, but it has following defects: it cannot destroy cells of different kinds simultaneously. The container must be open so that an ultrasonic horn may be put in the container. In this connection there is fear of scattering of aerosol from the open mouth of the container. This is most dangerous to persons in handling virus and other infectious agents. Also, there is fear of contamination of cells with bacteria. Sometimes water leaks, and the PH value varies.

In an attempt to solve these problems the inventor proposed an ultrasonic cell-destroyer as shown in FIGS. 9 and 10. It is shown as comprising a plurality of closed containers 1', each containing a given quantity of solution in which cells to be destroyed are suspended, and an elongated metal rod 2', and a vessel 3' containing a quantity of liquid W and being equipped with an ultrasonic generator (not shown) at its bottom. As shown, the containers 1' are partly soaked in the bath of the vessel 3'. In operation the metal rods 2' are subjected to the ultrasonic wave, and the rods 2' are resonant with the ultrasonic sound to break the membranes of the cells and remove their organs.

This ultrasonic cell-destroyer permits destruction of a relatively small quantity of cells of different kinds at one time. The containers are closed, and therefore there is no fear of scattering of aerosol, and there is neither leakage of water nor variation of PH value. Still advantageously, no physical factors will vary with time and temperature. It, however, has following defects:

(1) A very small quantity of cell sample, for instance ranging from 50 to 250 microliters, cannot be subjected to ultrasonic destruction because the use of a metal rod of substantial size prevents the size of the container from reducing to the extent that cells may be exposed to the vibration caused by the metal rod in the container.

(2) The presence of the metal rod in the container makes it difficult to subject the solution in the container to centrifugal separation.

SUMMARY OF THE INVENTION

With the above in mind one object of the present invention is to provide an ultrasonic cell-destroyer which permits destruction of even a very small quantity of cell sample in a closed container.

Another object of the present invention is to provide an ultrasonic cell-destroyer which facilitates subsequent centrifugal separation.

Still another object of the present invention is to provide an ultrasonic cell-destroyer which is capable of generating ultrasonic impacts against cells at an increased efficiency and destroying the cells without fail.

Still another object of the present invention is to provide an ultrasonic cell-destroyer which is capable of destroying equally the cells in a plurality of containers.

To attain these objects an ultrasonic cell-destroyer comprising at least one closed container comprising a container body and a closure for containing a given quantity of liquid in which cells to be destroyed are suspended, and a vessel equipped with ultrasonic wave generator means at its bottom so as to radiated ultrasonic wave to the container partly soaked in the bath of the vessel, is improved according to the present invention in that the container body has an upward converging groove on its bottom.

The container body may have a tapering shape converging towards its bottom end. The bottom end on which a groove is formed, may have a semi-spherical shape.

In order to permit the simultaneous destruction of the cells contained in a plurality of containers the apparatus may comprise a rotatable disk having the plurality of apertures in which the containers are to be fitted, the disk being laid above the surface of the bath in the vessel, and means for rotating the disk slowly, thereby permitting the containers to travel a circular paths while being exposed to the radiation of ultrasonic wave in the bath. Said means for rotating the disk slowly may be an electric motor. Or otherwise, it may be a manually operating device. The disk may comprise circular floor and ceiling plates and circumferential wall integrally connected to the floor plate. The floor plate has a plurality of apertures in which the containers are to be fitted, and the ceiling plate is used as a closure to define a closed space along with the floor plate and the circumferential wall. Then, the clearance between the ceiling and the top surface of the closure of the container, provides a space which permits efficient generation of resonance from ultrasonic energy in the container, thereby making full use of the ultrasonic energy to destroy the cells in the container.

In use a small quantity of solution in which cells are suspended, is put in each container, and then it is closed with its closure. A plurality of closed containers are partly soaked in the bath in the vessel so that the level of solution in each container may be lower than the surface of the bath. Then, ultrasonic generator means is operated to radiate ultrasonic wave to the bath. It is supposed that the destruction of cells in the containers is caused by:

(1) Bach closed container has a resonant vibration at its intrinsic or natural frequency, thereby causing the secondary vibration in the solution in the container. Thus, cavitation is caused in the solution to destroy the cells and remove their organs.

(2) When each closed container is exposed to ultrasonic wave, it vibrates vigorously, and accordingly the cells are repeatedly struck against the inner surface of the container. Thus, the cells are destroyed, and their organs are removed.

Each container has an upward converging or concave groove at its bottom, and the ultrasonic energy is apt to converge to the reentrant portion of the bottom of the container. The solution in which cells to be destroyed are suspended, are put in the bottom portion of the container, and therefore effective destruction can be performed. The rod-free container is useful in destroying a very small amount of cell in the solution, and it facilitated subsequent centrifugal separation. In case of fitting a plurality of containers in the apertures of a rotary disk, cells suspended in the solutions in these containers can be equally destroyed.

Other objects and advantages of the present invention will be understood from the following description of preferred embodiments which are shown in the accompanying drawings:

FIG. 1 is a longitudinal sectional view of the ultrasonic cell-destroyer;

FIG. 2 is a longitudinal sectional view of a closed container;

FIG. 3 is an enlarged longitudinal sectional view of the bottom part of the closed container of FIG. 2;

FIG. 4 is a longitudinal sectional view of another example of closed container.

FIG. 5 is a longitudinal section view of the ultrasonic cell-destroyer;

FIG. 6 is a plane view of the ultrasonic cell-destroyer;

FIG. 7 is a longitudinal sectional view of the part of the apparatus at which a container is mounted;

FIG. 8 is a perspective view, showing how a holder rod is fitted in an associated disk.

Figure 1:
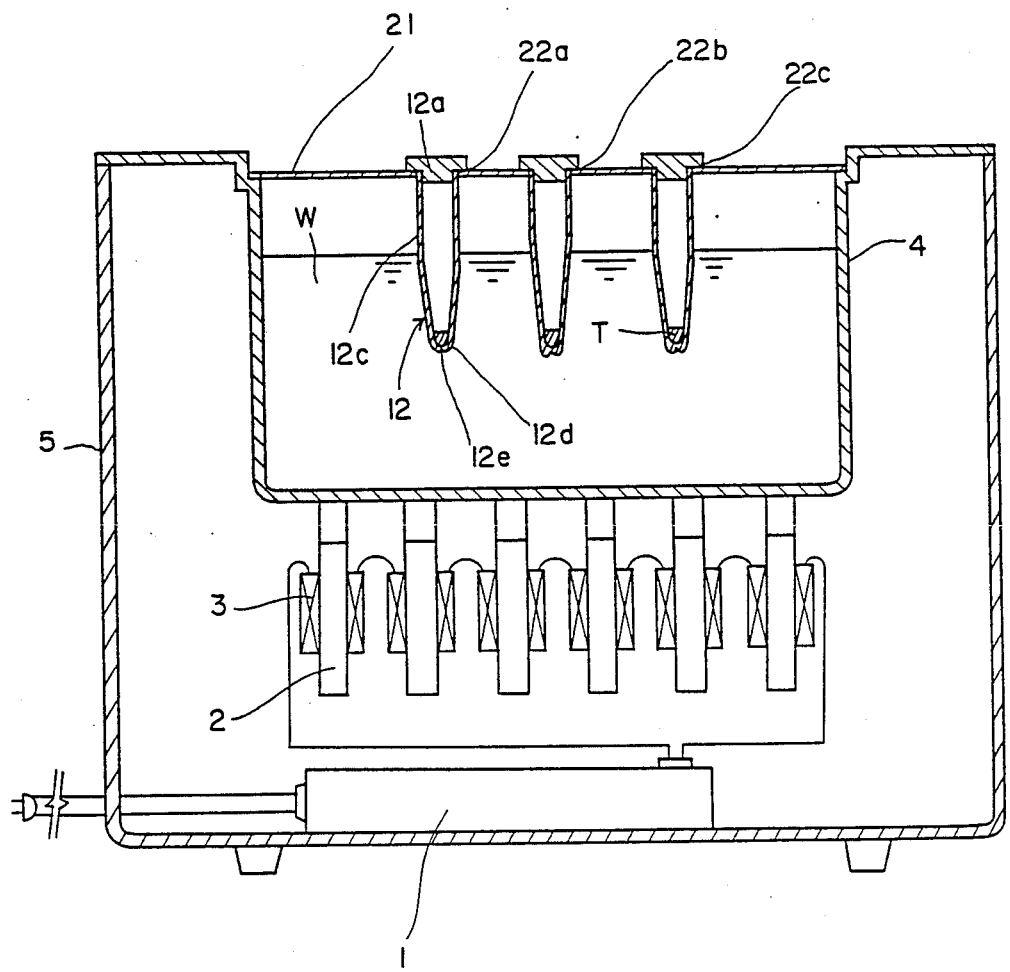
FIGS. 1 to 4 show an ultrasonic cell-destroyer according to the first embodiment of the present invention; specifically.

Referring to FIGS. 1 to 4, there is shown an ultrasonic cell-destroyer according to the first embodiment of the present invention.

It is shown as comprising, in a casing 5, a high-frequency oscillator 1, vibrating elements 2 such as ferrite magnetostriction vibrating elements each equipped with a driving coil 3, which is energized by the high-frequency oscillator 1, and a vessel 4 filled with liquid W.

The essential feature of the present invention resides in that: a closure plate 21 has a plurality of apertures 22a, 22b, 22c, . . . made therein, and a closed container 12 is fitted in each aperture. Each closed container comprises a closure cap 12a and a container body 12c with an upward converging groove 12e on its bottom 12d.

Figure 2:
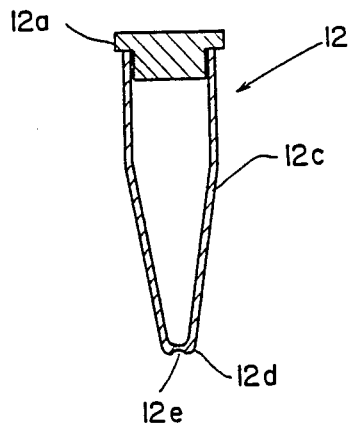
Figure 3:
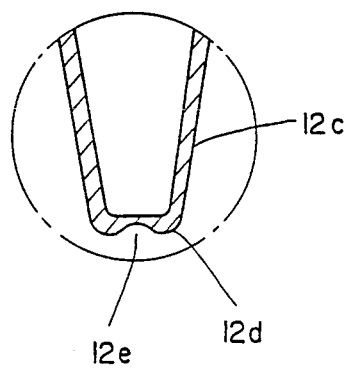
Figure 4:
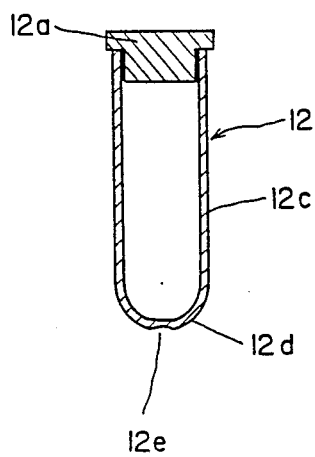

One example of the container as shown in FIGS. 2 and 3 has a container body 12c generally tapering to its bottom end 12d, and the bottom end has an upward concave groove 12e. Another example of the container as shown in FIG. 4 has a container body 12c rounded at its bottom end 12d, and likewise, the bottom end 12d has an upward concave groove 12e.

The container body 12c may be preferably made of a very hard material, and it can be made of polymethylpentene resin, polypropylene, acrylics, high-density polyethylene or polystyrene.

In use, cells to be destroyed are put in a solution, and then the solution is put in a container body 12c. The solution is indicated at T. The container body 12c is closed with a closure cap 12a. A plurality of containers thus filled with solution are fitted in the apertures 22a, 22b, 22c. Then, these containers are partly soaked in the liquid bath W in the vessel 4 so that the level of the solution T in each container may be brought under the surface of the bath W. Then, the ultrasonic oscillator is operated to radiate ultrasonic wave into the bath.

It is supposed that each container is vibrated at its intrinsic or natural frequency, and that the resonance of the container body generates the secondary vibration in the solution T in the container body, thereby causing cavitation in the solution to destroy the cells. Otherwise, it is supposed that the resonance of the container body causes the solution T in the container to vigorously vibrate, thereby repeatedly throwing cells against the inner surface of the bottom 12d of the container body 12c until they are destroyed. The upward concave 12e formed at the center of the bottom 12d of the container 12 has an effect to converge ultrasonic energy available to the center of the bottom 12d of the container 12. As a result the bottom 12d is supposed to be put in so vigorous vibration that the solution T is repeatedly thrown against the surrounding bottom wall of the container, thereby destroying cells, which are suspended in the solution.

As is seen the container 12 uses no rod, and therefore its size can be reduced to be appropriate for containing and destroying a very small quantity of cells. As a matter of course, the size of the rod-free container can be increased to meet destruction of a relatively large quantity of cells. Thanks to the absence of a rod in the container, it can be subjected to centrifugal separation subsequent to the ultrasonic destruction of cells, which is conducted around the upward convergent bottom of the container at an increased efficiency.

FIGS. 5 to 8 show an ultrasonic cell-destroyer according to the second embodiment of the present invention. In these drawings the same parts of the ultrasonic cell-vibrator as appear in FIGS. 1 to 4, are indicated by the same reference numerals, and explanation of these parts used in common are omitted. As shown, the ultrasonic cell-vibrator according to the second embodiment has a ceiling plate 6 integrally connected to its vessel 4. The ceiling plate 6 has a center opening. An electric motor 13 is mounted to the ceiling plate 6. A gear wheel plate 7 is rotatably laid across the center opening of the ceiling plate 6, and it is connected to the shaft of the electric motor 13 via an intermediate gear wheel 14. The gear wheel plate 7 has a holder rod 8 fixed thereto with nuts 16. Specifically, the holder rod 8 has threads at its upper and lower portions 8a and 8b. It is threadedly connected to the gear wheel plate 7 at its upper threads 8a to adjust the level at which a rotary container-holder 9 is held with respect to the surface level of the bath in the vessel, as later described in detail.

Figure 5:
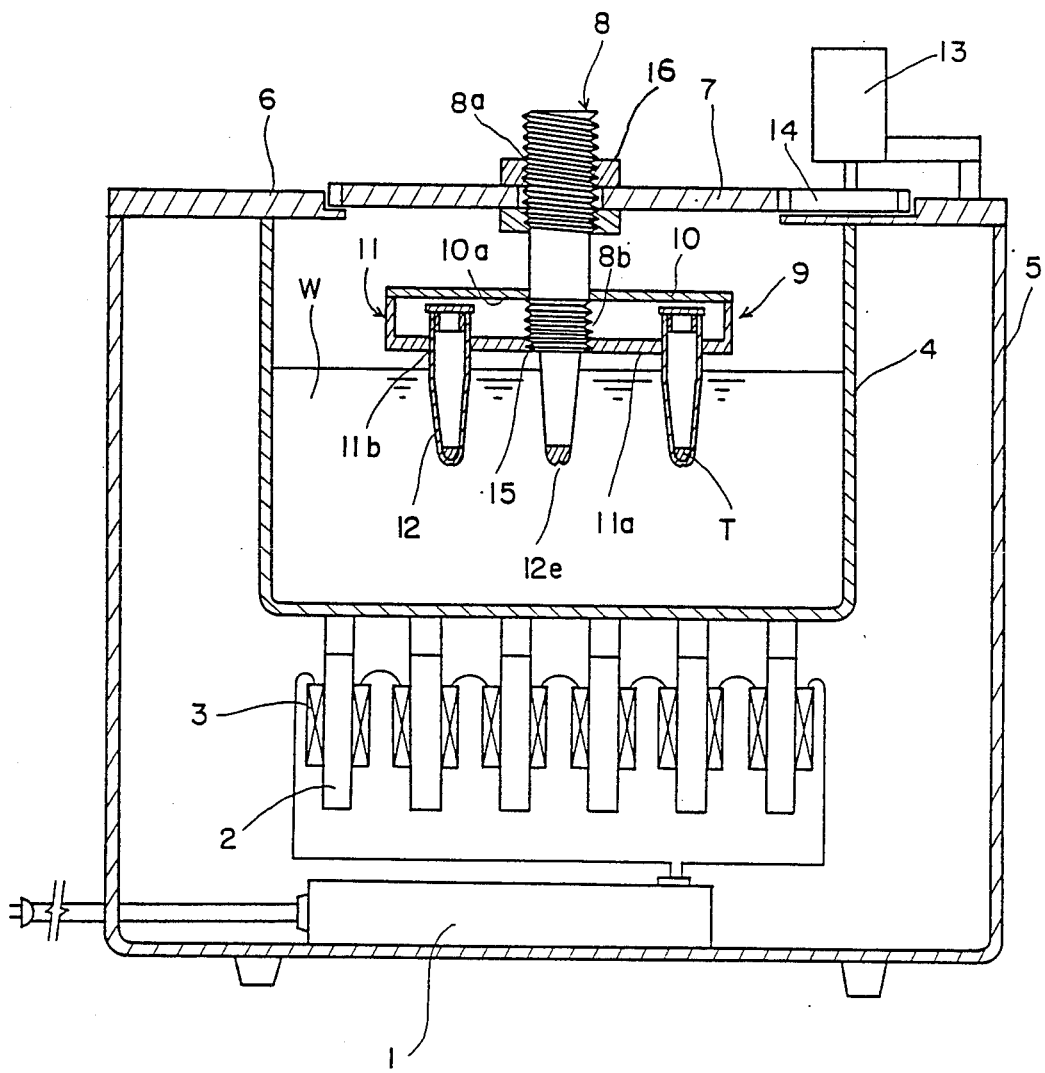
FIGS. 5 to 8 show an ultrasonic cell-destroyer according to the second embodiment of the present invention; specifically.
Figure 6:
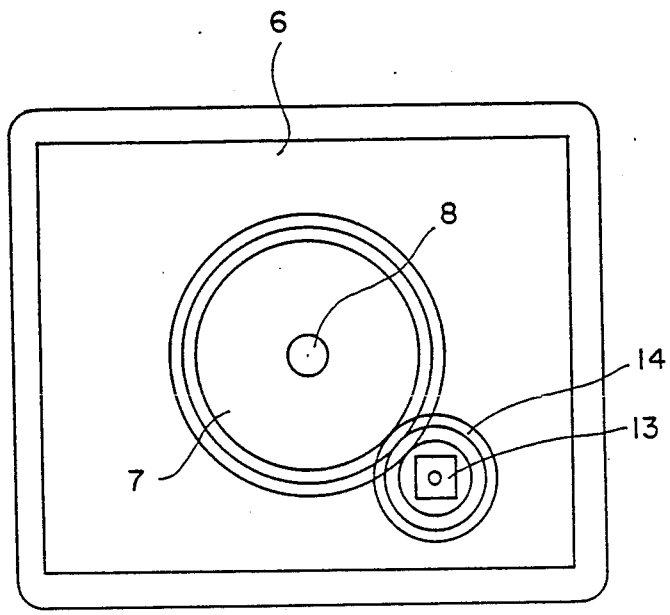
Figure 7:
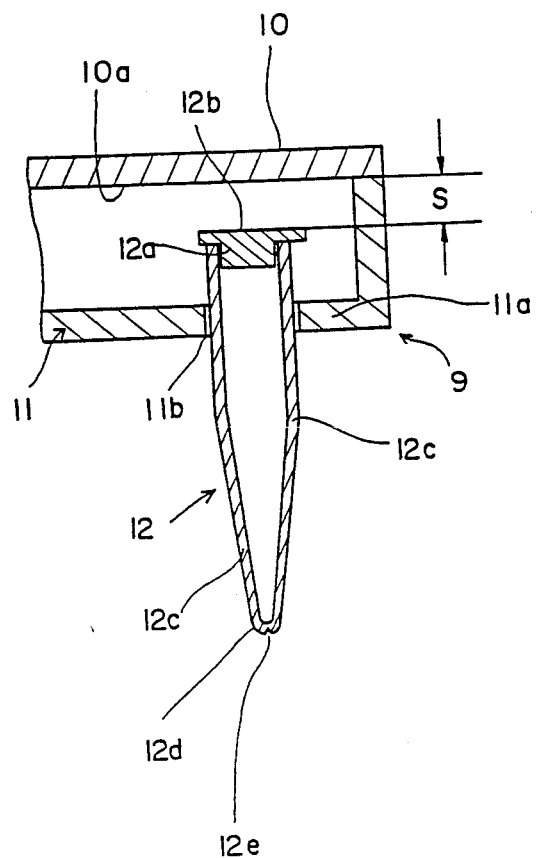
Figure 8:
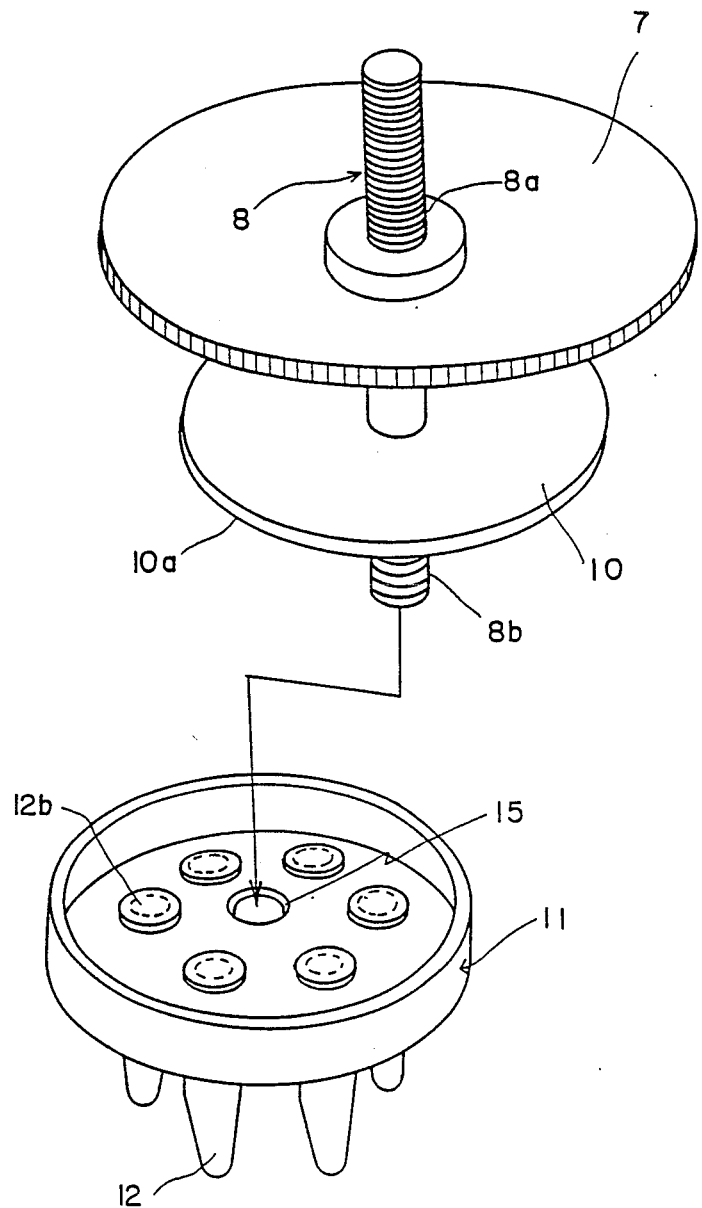
Figure 9:
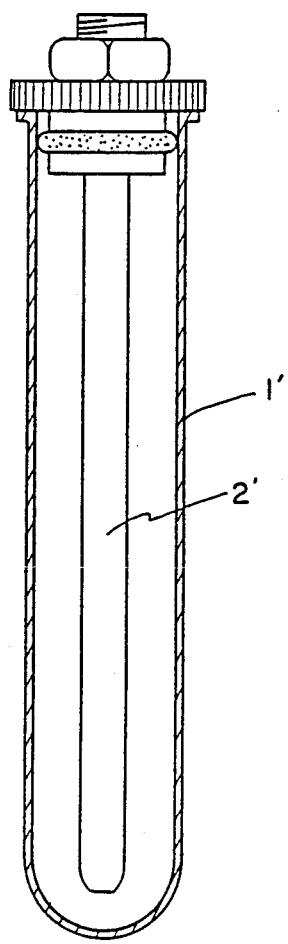
FIG. 9 is a longitudinal sectional view of a conventional closed container.
Figure 10:
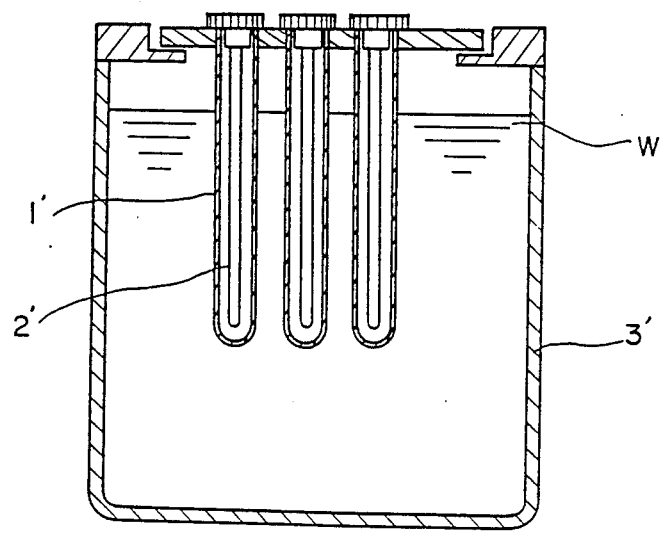
FIG. 10 is a longitudinal sectional view of a conventional ultrasonic cell-destroyer with closed container mounted.

The rotary container-holder 9 is circular in shape, and is smaller than the gear wheel plate 7 in diameter, and is threadedly engaged with the lower part of the holder rod 8. It comprises circular floor and ceiling plates 11a and 10 and circumferential wall 11 integrally connected to the floor plate 11a. The floor plate 11a has a plurality of apertures 11b in which the containers 12 are to be fitted. As shown, the ceiling plate 10 has a center hole to allow the lower length of the holder rod 8 to pass therethrough, and the floor plate 11a has center female-threaded hole to permit the lower male-threaded part 8b of the holder rod 8 to engage with the floor plate 11a as indicated at 15. As shown in FIGS. 5 and 7, the ceiling plate 10 is used as a closure to define a closed space along with the floor plate 11a and the circumferential wall 11, leaving the clearance S between the ceiling 10a and the top surface 12b of the container 12, thus providing a space which permits efficient generation of resonance from ultrasonic energy in the containers 12 to make full use of the ultrasonic energy to available to destroy cells in the containers 12.

In use, a solution in which cells to be destroyed are suspended, is put in a plurality of containers 12, and then these containers 12 are closed with their cap closures 12a. The ceiling plate is removed, and then the containers are fitted in the apertures 11b of the floor plate 11a.

Then, the ceiling plate 10 is put on the circumferential wall 11, and they are integrally connected by screwing the male-threaded lower part 8b of the holder rod 8 in the female-threaded hole 15 of the floor plate 11a.

As mentioned above, the clearance S is left between the ceiling 10a and the top surface 12b of the container 12 to provide a space which permits efficient generation of resonance from ultrasonic energy in the containers 12. The rotary container-holder disk having the containers 12 mounted therein is suspended from the gear wheel plate 7. Then, the containers are partly soaked in the bath W in the vessel 4 so that the level of the solution T in the containers 12 may be below the surface level of the bath W.

When the ultrasonic generator 2 is operated, the ultrasonic wave is transmitted in the bath W to reach the containers 12, causing these containers to vibrate at its resonant frequency to destroy cells in the containers 12 in the same way as in the ultrasonic cell-destroyer according to the first embodiment described above. It appears that thanks to the clearance S between the ceiling 10a and the top level of the closed containers 12 a strong resonance is caused in each closed container to produce cavitation in the solution and destroy cells therein.

The rotary container-holder 9 is rotated at a given constant velocity by the electric motor 13, thereby equally exposing the closed containers 12 to ultrasonic radiation, thereby assuring that cells in every container are evenly destroyed.

In this particular embodiment a plurality of apertures 11b in which containers 12 are to be fitted, are made in the floor plate 11a of the rotary container-holder 9. Alternatively, a plurality of apertures may be made in the gear wheel plate 7.

As is apparent from the above, an ultrasonic cell-destroyer according to the present invention uses no elongated rod to be put in a container in which cell-suspending solution is put, and therefore the container size can be reduced to be appropriate for the purpose of destroying a very small quantity of cell-suspending solution. The use of rod-free container facilitates subsequent treatment, such as centrifugal separation of destroyed cell. The groove of the container bottom permits convergence of ultrasonic energy to the center of the container bottom, thereby making full use of the ultrasonic energy available to destroy cells in the containers. Also, cells suspended in the solutions in a plurality of containers can be equally destroyed.

What is claimed is:

1. An ultrasonic cell-destroyer comprising at least one closed container 12 comprising a container body 12c and a closure 12a for containing a given quantity of liquid T in which cells to be destroyed are suspended, and a vessel 4 equipped with ultrasonic wave generator means at its bottom so as to destroy cells in the container 12, which is partly soaked in the bath W of the vessel 4, characterized in that the container body 12c has an upward converging or concave groove 12e on its bottom 12d.

2. An ultrasonic cell-destroyer according to claim 1 wherein the container body 12c has a tapering shape converging towards its bottom end 12d.

3. An ultrasonic cell-destroyer according to claim 1 wherein the bottom end 12d on which a groove is formed, has a semi-spherical shape.

4. An ultrasonic cell-destroyer according to claim 1 wherein it further comprises a rotatable disk 11 having a plurality of apertures 11b for snugly accommodating containers, the disk being rotatably mounted to the vessel, lying above the surface of the bath W in the vessel 4, and means for rotating the disk 11 slowly, thereby permitting the containers to travel circular pathes while being exposed to the radiation of ultrasonic wave in the bath.

5. An ultrasonic cell-destroyer according to claim 4 wherein said means for rotating the disk 11 slowly, is an electric motor.

6. An ultrasonic cell-destroyer according to claim 4 wherein said means for rotating the disk 11 slowly, is a manually operating means.

7. An ultrasonic cell-destroyer according to claim 4 wherein said disk 11 comprises circular floor and ceiling plates and a circumferential wall integrally connected to the floor plate, the floor plate having a plurality of apertures 11b in which the containers 12 are to be fitted, and the ceiling plate 10 being used as a closure to define a closed space along with the floor plate and the circumferential wall, the clearance S between the ceiling 10a and the top surface 12b of the closure 12a of the container 12 being determined to provide a space which permits efficient generation of resonance from ultrasonic energy in the container 12, thereby making full use of the ultrasonic energy to destroy the cells in the container 12.

* * * * *